United States Patent [19]

Afonso et al.

[11] 4,431,658
[45] Feb. 14, 1984

[54] AZA PENEM COMPOUNDS

[75] Inventors: Adriano Afonso, West Caldwell; Frank Hon, Paramus, both of N.J.

[73] Assignee: Schering Corporation, Kenilworth, N.J.

[21] Appl. No.: 387,726

[22] Filed: Jun. 11, 1982

Related U.S. Application Data

[62] Division of Ser. No. 230,774, Feb. 2, 1981, Pat. No. 4,347,183.

[51] Int. Cl.$^3$ .................. A61K 31/415; C07D 233/02
[52] U.S. Cl. .......................... 424/273 R; 260/245.2 R; 260/245.3
[58] Field of Search ..................... 260/245.2 R, 245.3; 424/270, 271, 273 R

[56] References Cited

U.S. PATENT DOCUMENTS 4,283,531  8/1981  Ganguly et al. ...................... 544/30

Primary Examiner—Nicholas S. Rizzo
Attorney, Agent, or Firm—Anita W. Magatti; Gerald S. Rosen; Bruce M. Eisen

[57] ABSTRACT

Described is a novel process for the preparation of penems and carbapenems useful as antibacterial agents which comprises the reaction of an appropriate 4-substituted-azetidine-2-one with an acid halide in the presence of a tertiary amine and an alkaline earth metal carbonate, followed by reaction of the thereby formed 1-imido-4-substituted-azetidine-2-one with a trialkyl phosphite.

Also described are novel penems useful as antibacterials which are prepared by the described process.

3 Claims, No Drawings

AZA PENEM COMPOUNDS

This is a division; of application Ser. No. 230,774, filed Feb. 2, 1981 now U.S. Pat. No. 4,347,183.

This invention relates to a novel process useful in the synthesis of penems and carbapenems having antibacterial activity and to novel compounds produced thereby.

More particularly, this invention relates to a process for preparing compounds of the following formula I:

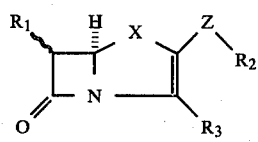

wherein $R_1$ is hydrogen, lower alkyl, acylamino or

wherein $R_4$ is hydrogen, lower alkyl, aryl, heteroaryl and $R_5$ is an O-protecting group;

$R_2$ is lower alkyl, aryl, aralkyl, an N-protected amino-lower alkyl, an O-protected hydroxyalkyl, thioalkyl, thioaryl, thioheteroaryl, an α-(N-protected) amino acid ester or an alkylcarboxylic acid ester;

$R_3$ is nitrile, tetrazole, or —$COOR_6$ wherein $R_6$ is lower alkyl, lower alkyltrihalogenomethyl, aryl, allyl, or a metabolisable ester such as phthalidyl or pivaloyloxymethyl;

X and Z are independently sulfur, oxygen, —$NR_7$ wherein $R_7$ is acyl, alkyl, aryl, N-protecting group, or —$(CH_2)_n$— wherein n is 1 or 2:

Those compounds of formula I wherein X is —$(CH_2)_n$— are identified as carbapenems whereas those compounds wherein X is sulfur, oxygen, or —$NR_7$ are identified as penems.

Compounds of formula I wherein the O-protecting and N-protecting groups have been removed are useful as antibiotics, being active against both gram positive organisms such as *Staphylococcus epidermis* and *Bacillus subtilis*, and such gram negative organisms as *E. coli* and Salmonella.

The lower alkyl groups referred to above for $R_1$, $R_2$, $R_4$ and $R_6$ contain 1 to 6 carbon atoms and are exemplified by methyl, ethyl, propyl, butyl, pentyl, hexyl, and the corresponding branched-chain isomers thereof.

The acyl portion of the acylamino substituents referred to above for $R_1$ denotes groups of the formula

wherein $R_8$ is lower alkyl, aralkyl, lower alkoxy, aryloxy, alkenyl or alkynyl of 2–6 carbon atoms, cycloalkyl of 4–6 carbon atoms, heteroaryl, heteroaralkyl, optionally substituted by hydroxy, thiol, alkylthio, lower alkyl, lower alkoxy, halogen, cyano, carboxy, nitro, amino, aminoloweralkyl or haloloweralkyl such as trifluoromethyl. Representative of such groups are those such as benzyl, p-hydroxybenzyl, 4-amino-4-carboxybutyl, methyl, cyanomethyl, 2-pentenyl, n-amyl, p-heptyl, ethyl, 3- or 4-nitrobenzyl, phenethyl, α,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl), 5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, p-carboxymethylbenzyl, m-fluorobenzyl, m-bromobenzyl, p-chlorobenzyl, p-methoxybenzyl, 1-napthylmethyl, 3-isothiazolylmethyl, 4-isothiazolylmethyl, 5-isothiazolylmethyl, 4-pyridylmethyl, 5-isoxazolymethyl, 4-methoxy-5-isoxazolylmethyl, 4-methyl-5-isoxazolylmethyl, 2-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl) vinyl, phenyl, o-methoxyphenyl, o-chlorophenyl, o-phenylphenyl, p-aminomethylbenzyl, 1-(5-cyanotrizolyl)methyl, difluoromethyl, dichloromethyl, dibromomethyl, 1-(3-methylimidazolyl)methyl, 2- or 3-(4-carboxymethylthienyl)methyl, 2- or 3-(5-methylthienyl)methyl, 2- or 3-(methoxythienyl)methyl, 2- or 3-(4-chlorothienyl)-methyl, 2- or 3-(5-carboxythienyl)methyl, 3-(1,2,5-thiadiazolyl)methyl, 3-(4-methoxy-1,2,5-thiadiazolyl)-methyl, 2-furylmethyl, 2-(5-nitrofuryl)methyl, 3-furylmethyl, 2-thienylmethyl, 3-thienylmethyl, tetrazolylmethyl, cyclohexylamidinomethyl and other similar acyl groups found in conventional penicillin derivatives. The term also denotes an acyl residue derived from an α-amino acid of the L or D configuration.

The term "aryl" as used herein for $R_1$, $R_2$, $R_4$ and $R_6$ refers to phenyl optionally substituted by lower alkyl, lower alkoxy and halogen groups, e.g., p-tolyl, o-tolyl, m-tolyl, p-chlorophenyl, o-methoxyphenyl, etc. Halogeno refers to a fluorine, chlorine, bromine or iodine substituent.

The term "heteroaryl" as used herein for $R_5$ refers to aryl groups having a hetero atom in the ring such as pyridyl, furanyl, thienyl or the like. The heteroaryl group may optionally contain 1 to 3 lower alkyl substituents, e.g., 2-methylpyridyl, 3-methylthienyl, etc. Where there is a possibility of the various position isomers, the term "heteroaryl" is intended to cover all isomers, e.g., 2-pyridyl, 3-pyridyl and 4-pyridyl.

The term "aralkyl" denotes lower alkyl groups substituted by one or more aryl groups such as benzyl, phenethyl, benzhydryl and the like.

The term "metabolisable ester" group denotes an ester group which is metabolically removed in the body. Two particularly useful metabolisable ester groups are the phthalidyl group and the pivaloyloxymethyl group.

Amine protecting groups, designated herein as N-protecting groups, and hydroxyl protecting groups, designated herein as O-protecting groups, are well known in the art as well as their methods of preparation and removal.

Preferred N-protecting groups for use in the process of this invention to protect amine substituents included within the definitions of $R_2$, X and Y in formula I are groups such as 2,2,2-trichloroethoxycarbonyl, benzhydryloxycarbonyl or, preferably, allyl oxycarbonyl.

Preferred hydroxyl protecting groups for use in the process of this invention to protect hydroxyl substituents included within the definitions of $R_2$ and $R_5$ in formula I are groups such as 2,2,2-trichloroethoxycarbonyl, 1,1,1-trichloro-2-methyl-2-propoxycarbonyl, p-nitrobenzyloxycarbonyl or allyloxycarbonyl, with 2,2,2-trichloroethoxycarbonyl being preferred.

Compounds of formula I wherein X is sulfur and wherein the O- and N-protecting groups have been removed are known as antibacterial agents being described, for example, in European Published Application Nos. 13,662; 2,210 and 3,960.

Additionally, carbapenems of formula I (i.e. compounds wherein X is $-(CH_2)_n-$ and penems of formula I wherein X is oxygen are known antibacterial agents being described, for example, by B. G. Christensen, et. al., J. Chem. Soc. 100, 8006, (1978), and P. H. Bentley, et. al., Chem. Soc., Chemical Communications, P. 905 (1977) and P. 518 (1978).

Novel compounds of formula I include those penem derivatives wherein X is $-NR_7$ and O- and N-deprotected analogs thereof. Thus, included within our inventive concept are compounds of the following formula II:

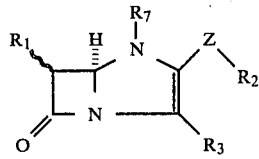

wherein $R_1$ is hydrogen, lower alkyl, acylamino or

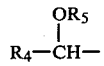

wherein $R_4$ is hydrogen, lower alkyl, aryl, heteroaryl, and $R_5$ is hydrogen or an O-protecting group;

$R_2$ is alkyl, aryl, aralkyl, aminoalkyl, an N-protected-lower amino-alkyl, hydroxyalkyl, an O-protected hydroxyalkyl, thioalkyl, thioaryl, thioheteroaryl, an $\alpha$-amino acid ester an $\alpha$-(N-protected) amino acid ester or an alkyl carboxylic acid ester;

$R_3$ is nitrile, tetrazole, or $-COOR_6$ wherein $R_6$ is lower alkyl, lower alkyltrihalogenomethyl, aryl, allyl, a metabolisable ester such as phthalidyl or pivaloyloxymethyl, hydrogen or an alkali metal cation;

Z is sulfur, oxygen, $-(CH_2)_n-$ wherein n is 1 or 2, or $-NR_7$ wherein $R_7$ is hydrogen, acyl, alkyl, or aryl, or an N-protecting group; and the pharmaceutically acceptable salts thereof.

Compounds of formula II wherein $R_7$ is an N-protecting group and which have other N- and O-protecting groups are products of our novel process described hereinbelow which, when the O- and, optionally, the N-protecting groups have been removed, produce compounds wherein $R_7$ is hydrogen and other protecting groups are replaced by hydrogen, and which exhibit antibacterial activity.

Thus, another aspect of our invention includes within its scope pharmaceutical compositions comprising an antibacterially effective amount of a penem of formula II wherein $R_7$ is hydrogen, acyl, alkyl, or aryl and all O- and optionally, all N-protecting groups have been removed together with a compatible, pharmaceutically acceptable carrier or coating. Also included within this invention is the method of eliciting an antibacterial response in a warm-blooded animal having a susceptible bacterial infection which comprises administering to said animal a non-toxic, antibacterially effective amount of a compound of formula II wherein $R_7$ is hydrogen, acyl, alkyl or aryl and all O- and optionally, N-protecting groups have been removed.

The dosage administered of the penems of this invention is dependent upon the age and weight of the animal species being treated, the mode of administration, and the type and severity of bacterial infection being prevented or reduced. Typically, the dosage administered per day will be in the range of 100–5000 mg, with 500–1000 mg being preferred.

For oral administration, the antibacterial compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, or in the form of creams.

The compounds of formula II wherein $R_7$ is hydrogen, acyl, alkyl, or aryl, and wherein all O- and optionally, N-protecting groups have been removed may be utilized in liquid form such as solutions, suspensions and the like for otic and optic use and may also be administered parenterally via intramuscular injection.

Preferred compounds of formula II are those wherein $R_1$ is

and Z is sulfur, particularly those wherein $R_2$ is lower alkyl or amino-lower alkyl.

The compounds of formula I and II possess several centers of chirality and the process of this invention, depending on the configuration of the starting compound, will produce either chiral compounds of a specific configuration or isomeric mixtures.

A preferred aspect of this invention is directed to a process for preparing compounds of formula I wherein $R_1$ is

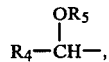

$R_2$ is methyl or ethyl and Z and X is sulfur, particularly the preparation of the foregoing compounds wherein $R_4$ is methyl. The preferred configuration of the foregoing compounds is that wherein the configuration at C-5 and C-6 of the absolute stereochemistry R and S, respectively. The two hydrogen atoms attached to the 5 and 6 carbon atoms are thus trans to one another. The stereochemistry of the C-8 carbon atom (i.e. the carbon atom of the

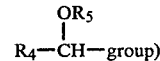

may be designated as either R or S depending on the exact nature of the $R_2$ substituent. For instance, the compounds wherein $R_4$ is methyl will have the 8R stereochemistry. The most preferred embodiment of the process aspect of this invention is, therefore, directed to the preparation of compounds of the following formula III, having a stereoconfiguration designated 5R,6S,8R and having the following representative spatial configuration

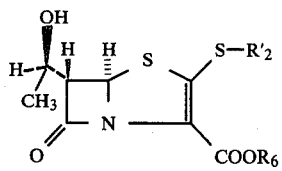

wherein $R_2^1$ is methyl or ethyl.

DETAILED DESCRIPTION OF THE PROCESS ASPECT OF THE INVENTION

The compounds of formula I are prepared by the process of this invention which comprises the reaction of an azetidinone of formula A:

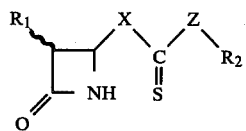

wherein $R_1$, $R_2$, X and Z are as hereinabove defined for formula I, with an acid halide of formula B:

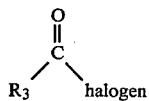

wherein $R_3$ is as hereinabove defined for formula I, in an inert solvent in the presence of a tertiary amine and an alkaline earth metal carbonate; followed by reaction of the thereby produced imido derivative of formula C:

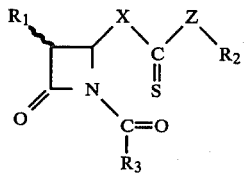

wherein $R_1$, $R_2$, $R_3$, X and Z are as hereinabove defined for formula I.

with a trialkyl phosphite, said reaction being carried out at temperatures in the range of from about 20° to about 80° C.

Our process is conveniently carried out in an inert solvent. By "inert solvent" is meant any organic or inorganic solvent is which the starting compound and reagents are soluble, and which will not interfere with the process under the reaction conditions thereof, so there are produced a minimum of competing side reactions. Inert solvents which may be used in our process include aromatic hydrocarbons (e.g. benzene, toluene and the like), aliphatic ethers (e.g. diethyl ether, dipropyl ether), cyclic ethers (e.g. dioxane, tetrahydrofuran) and, preferably halogenated hydrocarbons such as methylene chloride and chloroform.

In general those inert solvents are preferred (e.g. halogenated hydrocarbons) which have the solubility characteristics discussed hereinabove and which have a boiling point in the range of about 40° to 80° C. so that the same solvent may be used in both steps of our process and the entire process may be advantageously carried out in one vessel without the necessity of isolating the imido intermediate, C, of the first step of the process.

In general, when carrying out the process of this invention, the first step comprises the reaction of an azetidinone of formula, A, in an inert solvent (as defined hereinabove), usually at temperatures in the range of from about 5° to about 25° C., preferably from 10° C. to 15° C., with about an equimolar amount of each of an acid halide of formula B and a tertiary amine in the presence of an alkaline earth metal carbonate, preferably calcium carbonate, in an amount which is at least equimolar (and preferably is in excess of equivalent) to the azetidinone of formula A.

Any tertiary amine (e.g. triethylamine) may be used in our process with di-isopropyl-ethyl amine being preferred.

In carrying out this first step of our process, usually about 1.2 moles of each of the tertiary amine and acid chloride, B, and a large excess of calcium carbonate (e.g. 10 moles) are used per mole of azetidinone, A, with a molar ratio of solvent of azetidinone, A, being 10 to 1.

The first step of the process is followed by thin layer chromatography (TLC) until TLC shows no starting material. At that point, the reaction solution containing imido intermediate, C, may be filtered to remove the alkaline earth metal carbonate and the filtered solution washed with water to remove the tertiary amine acid halide salt formed during the reaction then dried, and diluted with additional inert solvent prior to reaction with a trialkylphosphite. Alternatively, the reaction mixture may be diluted directly with additional inert solvent so that the molar ratio of starting azetidinone, A, (and thus, also, of the imido intermediate, C,) to solvent is about 1 to 50.

In the second step of our process, to the imido intermediate, C, in solution in an inert solvent there is added a solution of about two molar equivalents of a trialkylphosphite (usually triethylphosphite) in an inert solvent, with the reaction solution being maintained at temperatures in the range of from about 20° C. to about 80° C., usually from 40° C. to about 60° C., and preferably at 60° C., usually from about 6 to about 24 hours.

Greater yields of N- and O-protected penems and carbopenems of formula I are obtained when the addition of trialkylphosphite solution is carried out during a period of from about 2 to 3 hours. Best yields of the product of formula I are also obtained when the reaction is carried out at 40° to 60° C.

When T.L.C. shows the absence of imido intermediate, C, the desired product, (i.e. compound of formula I) is isolated and purified via conventional techniques, usually chromatographic techniques followed by crystallization.

A preferred embodiment of our process, i.e. of preparing N- and O-protected derivatives of formula III, is shown via flow diagram as follows:

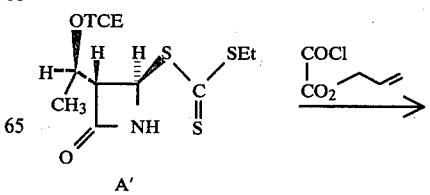

-continued

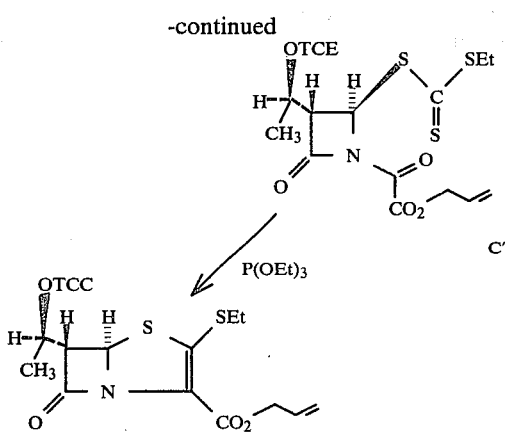

I'

In carrying out this preferred mode of our inventive process, to the azetidinone of formula A[1] (which is a compound of formula A where $R_1$ is

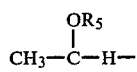

wherein $R_5$ is the O-protecting group trichlorethoxycarbonyl) having the stereoconfiguration 3S,4R,5R, in a chloroform solution at 10° C. to which has been added an excess of calcium carbonate, there is added about 1.2 molar equivalents of allyloxalylchloride (i.e. a compound of formula B wherein $R_3$ is carboxyallyl) followed by about 1.2 molar equivalents of di-iso-propylethylamine in methylene chloride. After 15 minutes reaction time, the excess calcium carbonate is filtered off, the organic solution is washed with water, and chloroform is added to make a 50 to 1 ratio of chloroform to starting compound, thence, to the chloroform solution of the imido intermediate C[1] at reflux temperature, there is added over a 3 hour period a solution of 2 equivalents of triethylphosphite in chloroform. After refluxing an additional 18 hours, the desired compound of formula I[1], i.e. allyl-(5R,6S,8R)-6-(1-triethoxycarbonyloxyethyl)-2-(ethylthio)penem-3-carboxylate is isolated via chromatography on silica gel and crystallization from ether-hexane.

The foregoing intermediate is conveniently converted to a penem of formula III by removing the O-protecting group at C-8 (i.e. the trichlorethoxycarbonyl) by known procedures, e.g. via zinc/acetic acid; and removing the allyl protecting group of the 3-carboxylic acid function. The allyl group is most preferably removed by the procedure of McCombie, described in E.P.O. Published Application No. 0013662. The McCombie deprotection procedure utilizes a suitable aprotic solvent, such as tetrahydrofuran, diethyl ether or methylene chloride, with potassium or sodium 2-ethylhexanoate or 2-ethylhexanoic acid and a mixture of a palladium compound and triphenyl phosphine as the catalyst. This deprotection method is particularly suitable for the sensitive beta-lactam carboxylates of this invention. Use of the potassium or sodium 2-ethylhexanoate provides the corresponding salt, while use of 2-ethylhexanoic acid affords the free carboxy, amine or hydroxy group.

The foregoing preferred process species of our invention represents a great improvement over prior art methods of converting the azetidinone, A, to the penem I, and specifically to the penems of formula III. By our process, this conversion is effected in two steps, via a one vessel reaction which is completed in less than a day and results in good yields of pure product. By prior art methods, such as described in E.P.O. Published Applications 13,662; 3,960; and 2,210, and specifically via the "Woodward method" (Journal of American Chemical Society, 100:26. 8214 (1978), which conversion requires 4 steps in each of which the product must be isolated and purified prior to continuing on to the next step, which requires well over a week to complete, with a resulting product which is a mixture of compounds requiring several chromatographic purifications before the desired penem of formula III is isolated in pure form.

The starting intermediates for my process are either known compounds or are prepared by procedures known in the art. Thus, azetidinones of formula A wherein X is sulfur, such as described in further detail in the Preparations and Examples and in the discussion of the preferred process species of this invention are described in E.P.O. Published Application Nos. 13,662; 3,960 and 2,210. Other azetidinone starting compounds are also known or are prepared via known procedures.

The following Preparations and Examples describe in detail the process of the present invention. It will be apparent to those skilled in the art that many modifications may be practiced without departing from the spirit and scope of the invention. Throughout these Preparations and Examples, "NMR" denotes nuclear magnetic resonance spectra; "rotation" denotes optical rotation of the compounds in a suitable solvent; "MS" denotes mass spectra; "UV" denotes ultraviolet spectra; and "IR" denotes infrared spectra. Chromatography is performed on silica gel unless otherwise noted.

PREPARATION A

ALLYL OXALYL CHLORIDE

Allyl alcohol (11.6 g) is added dropwise with stirring to a cold (0° C.) solution of oxalyl chloride (25.4 g.) in dry ether (50 ml.) while maintaining the temperature of the reaction mixture during the addition at 10°–12° C. The reaction mixture is then stirred overnight followed by removal of the solvent in a rotary evaporator. The resultant residue is distilled to yield allyl oxalyl chloride as a colorless liquid (16 g.), b.p. 68°–70° C./44 mm.

PREPARATION B (3S,4R,5R)-3-(1-TRICHLOROETHOXYCARBONYLOXY-ETHYL)-4-[(ETHOXY)CARBONOTHIOYLTHIO]-AZETIDIN-2-ONE

To a solution of ethanol (50 ml.) containing 1-N sodium hydroxide (10 ml.) add carbon disulfide (4 ml.) dropwise, stir ten minutes, then add dropwise to a solution of (3S,4R,5R)-[1-(2-methoxy-1,2-dioxoethyl)]-3-(1-trichloroethoxycarbonyloxyethyl)-4-chloroazetidin-2-one (4.1 g.) in ethanol. Stir the reaction mixture until t.l.c. analysis indicates no starting compound is present (about 4 hours) then dilute with ethyl acetate, wash the solution with saturated sodium chloride, dry the solution over magnesium sulfate, evaporate, and chromatograph the resulting residue on silica gel (40 g.) eluting with 30% ether-hexane. Combine the like elutes as determined by the t.l.c. and evaporate to a residue which is the title compound. I.R.=5.65μ;

NMR: δ 5.5 ppm (1H,d,J=2 cps) 3.4 ppm (1H,q,J=8 and 2 cps).

EXAMPLE 1

ALLYL (5R,6S,8R)-6-(1-TRICHLOROETHOXY-CARBONYLOXYETHYL)-2-ETHYLTHIO-2-PENEM-3-CARBOXYLATE

To a solution of (3S,4R,5R)-3-(trichloroethoxycarbonyloxyethyl)-4[(ethylthio)-carbonothioylthio]-azetidine-2-one (0.628 g.) in methylene chloride (6 ml) cooled to 10° C., add, with stirring, calcium carbonate (0.6 g) followed by allyloxalyl chloride (0.263 g, 1.2 eq.). Add dropwise a solution of diisopropylethylamine (0.32 ml, 1.2 eq.) in methylene chloride (1 ml), during 5 mins. while maintaining the temperature at 10°-15° C. After TLC shows no starting compound (15 mins) at 15° C., the mixture transfers to a separatory funnel using ethanol-free chloroform. Wash twice with ice/water, filter to remove excess calcium carbonate, dry over anhydrous sodium sulfate, and transfer to a 100 ml 3-neck flask. Adjust the volume of the solution to approximately 50 ml with chloroform and heat at reflux temperature while adding a solution of triethylphosphite (0.6 ml, 2 eq.) in chloroform (20 ml) over a 3 hour period. Reflux the mixture for an additional 18 hours, evaporate and chromatograph on 14 g silica gel, eluting with 25% ether-hexane, and evaporating the combined like elutes to obtain a residue (420 mg) comprising the title compound (58% yield). Purify by crystallization from ether-hexane to obtain the title compound in crystalline form. Yield 330 mg (46% theory).

EXAMPLE 2

ALLYL (5R,6S,8R)-6-(1-TRICHLOROETHOXYCARBONYLOXYETHYL)-2-ETHOXY-2-PENEM-3-CARBOXYLATE

Add allyloxlylchloride (0.52 g.) with stirring to a cold solution of (3S,4R,5R)-3-(1-trichloroethoxycarbonyloxyethyl)-4-[ethoxy)-carbonothioylthio]-azetidin-2-one in methylene chloride (10 ml) containing calcium carbonate (1.0 g). Add a solution of di-isopropyl-ethylamine (0.62 ml) in methylene chloride (2 ml) to this reaction solution at a rate so as to maintain the reaction temperature between 10°-15° C. After 15 mins. wash the solution 2 times with cold saturated sodium chloride, filter, dry, transfer to 3-neck flask and dilute to 45 ml with methylene chloride. Reflux the solution while adding a solution of triethylphosphite (1.3 ml) in methylene chloride (15 ml) over a period of 3.6 hours. Allow the reaction mixture to reflux for an additional 17 hours, cool and evaporate. Chromatograph the resulting residual oil on 30 g. silica gel, eluting with 35% ether-hexane to obtain the title compound. Purify by crystallization from ether-hexane to obtain colorless needles (300 mg.) mp 84°-85° C. $[\alpha]_D + 167°$ (chloroform).

I.R.: 5.60, 5.75μ NMR (CDCl$_3$) 85.55 ppm (d, 1H, J 1.5 cps) 4.22 ppm (q. 2H).

MS: M+ 474.

In a manner similar to that described in Examples 1 and 2, by starting with the appropriate azetidinone, there is obtained the title compounds and other compounds of formula I hereinabove, having the following stereochemistry: (5R,6S,8R), (5R,6R,8R), (5R,6S,8S), (5S,6S,8S), (5S,6S,8R) or racemic mixtures thereof.

We claim:

1. A compound having the following structural formula:

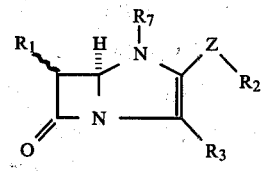

wherein $R_1$ is hydrogen; lower alkyl; $R_8$-C-amino wherein $R_8$ is lower alkyl, lower alkyl substituted by one or more of one or two ring carbocyclic aromatic groups, lower alkoxy, phenyloxy, alkenyl of 2 to 6 carbon atoms, alkynyl of 2–6 carbon atoms, cycloalkyl of 4–6 carbon atoms, unsubstituted or substituted heteroaryl or heteroarylloweralkyl wherein the heteroaryl contains one or two hetero atoms selected from oxygen, nitrogen or sulfur and wherein the substituents in the heteroaryl are from 1 to 3 lower alkyl groups, wherein said $R_8$ substituents are optionally substituted by hydroxy, thiol, loweralkylthio, lower alkyl, lower alkoxy, halogen, cyano, carboxy, nitro, amino, aminoloweralkyl or haloloweralkyl; or $$\underset{R_4-CH-}{\overset{OR_5}{|}}$$

wherein $R_4$ is hydrogen, lower alkyl, phenyl substituted by lower alkyl, lower alkoxy or halogen, heteroaryl wherein the heterocyclic ring is an aromatic heterocyclic containing a hetero atom selected from sulfur, oxygen or nitrogen, and $R_5$ is hydrogen or an O-protecting group;

$R_2$ is lower alkyl, phenyl substituted by lower alkyl, lower alkoxy or halogen, alkylaryl, aminoloweralkyl, an N-protected amino-lower alkyl, hydroxy lower alkyl, an O-protected hydroxyloweralkyl, thio lower alkyl, an α-amino acid ester, an α-(N-protected) amino acid ester or a lower alkyl carboxylic acid ester;

$R_3$ is nitrile, tetrazole, or —COOR$_6$ wherein R$_6$ is lower alkyl, loweralkyltrihalogenomethyl, phenyl substituted by lower alkyl, lower alkoxy or halogen, allyl, a metabolisable ester, hydrogen, or an alkali metal cation;

Z is sulfur, oxygen, —(CH$_2$)$_n$— wherein n is 1 or 2, or NR$_7$ wherein R$_7$ is hydrogen, lower alkyl, phenyl substituted by lower alkyl, lower alkoxy or halogen,

wherein R 8 is as defined above, or an N-protecting group;

and the pharmaeutically acceptable salts thereof.

2. A pharmaceutical composition comprising an antibacterially effective amount of a compound of claim 1 wherein R$_7$ is hydrogen,

wherein R 8 is as defined above, lower alkyl, or phenyl substituted by lower alkyl, lower alkoxy or halogen, and all O- and, optionally, all N-protecting groups have been removed, together with a non-toxic pharmaceutically acceptable carrier.

3. A method of eliciting an antibacterial response in a warm-blooded animal having a susceptible bacterial infection which comprises administering to said animal a non-toxic antibacterially effective amount of a compound of claim 1 wherein $R_7$ is hydrogen,

wherein $R_8$ is as defined in claim 1, lower alkyl, or phenyl substituted by lower alkyl, lower alkoxy or halogen, and all O- and, optionally, all N-protecting groups have been removed.

* * * * *

Notice of Adverse Decision in Interference

In Interference No. 101,315, involving Patent No. 4,431,658, A. Afonso and F. Hon, AZA PENEM COMPOUNDS, final judgment adverse to the patentees was rendered Aug. 5, 1985, as to claim 1.

[*Official Gazette July 15, 1986.*]